US005726031A

United States Patent [19]
Roth et al.

[11] Patent Number: 5,726,031
[45] Date of Patent: Mar. 10, 1998

[54] TEST MEDIA AND QUANTITATIVE METHOD FOR IDENTIFICATION AND DIFFERENTIATION OF BIOLOGICAL MATERIALS IN A TEST SAMPLE

[75] Inventors: Jonathan N. Roth, Goshen; Gordon L. Bontrager, South Bend, both of Ind.

[73] Assignee: RCR Scientific, Inc., Goshen, Ind.

[21] Appl. No.: 622,366

[22] Filed: Mar. 26, 1996

[51] Int. Cl.$^6$ .............. C12Q 1/04; C12Q 1/02; C12Q 1/54; C12Q 1/10
[52] U.S. Cl. .............. 435/34; 435/29; 435/7.37; 435/41; 435/14; 435/38; 435/849; 435/252.33; 435/252.1; 435/879; 536/1.11; 536/2; 536/114
[58] Field of Search .............. 435/34, 29, 7.37, 435/41, 14, 38, 849, 252.33, 252.1, 879; 536/1.11, 2, 114

[56] References Cited

U.S. PATENT DOCUMENTS

| | | | |
|---|---|---|---|
| 4,275,149 | 6/1981 | Litman et al. | 435/7 |
| 4,925,789 | 5/1990 | Edberg | 435/38 |
| 5,098,832 | 3/1992 | Rambach | 435/34 |
| 5,194,374 | 3/1993 | Rambach | 435/34 |
| 5,210,022 | 5/1993 | Roth et al. | 435/34 |
| 5,358,854 | 10/1994 | Ferguson | 435/14 |
| 5,364,767 | 11/1994 | Flowers et al. | 435/39 |
| 5,393,622 | 2/1995 | Roth et al. | 435/38 |
| 5,411,867 | 5/1995 | Chang et al. | 435/34 |
| 5,443,963 | 8/1995 | Lund | 435/34 |

OTHER PUBLICATIONS

Chuang, et al., "New Dye–Containing Media for Detection of *Escherichia coli* 0157:H7"; Book of Abstracts, 1995 IFT Annual Meeting, 81E–10, 253, month not available, please print.

Sales brochure; DIFCO Laboratories, "EZ Coli Rapid Foodborn Pathogen Detection System," 1995. Month not available.

Dynal Sales Brochure; "Dynabeads Anti–*E.coli* 157 the only selective enrichment procedure for E.Coli O157", 1995. Month not available.

Okrend, et al. "Use of 5–Bromo–4Chloro–3–Indoxyl–B–D–Glucuronide in MacConkey Sorbitol Agar", *Journal of Food Protection*, vol. 53, No. 11, pp. 941–953, Nov., 1990. Month not available.

Firstenberg–Eden, "A New Rapid Method for the Detection of *E.coli* 0157:h7 in Raw Meat", Program & Abstract Book, 69, 1995. Month not available.

Weagant, et al., "An improved Rapid Technique for isolation of *Escheria coli* 0157:H7 from Foods": *Journal of Food Protection*, vol. 58, No. 1, pp. 7–12, Jan. 1995. Month not available.

Sales Brochure, Oxoid Diagnostic Reagents, *E. coli* 0157 Latex Test, 1990. Month not available.

Ley, "Indoxyl–B–D glucuronide, a novel chromogenic reagent for the specific detection and enumeration of *Escherichia coli* in environmental samples", Can.J.Microbiol, 34, 690–693, 1987. Month not available.

Zomer, "E–Colite, The New Standard in Monitoring Coliforms and *Eschericia coli* Contamination in Water" Program and Abstract Book, 70,1995. Month not available.

Primary Examiner—Louise Leary
Attorney, Agent, or Firm—Baker & Daniels

[57] ABSTRACT

A test method and medium for quantitatively identifying and distinguishing biological materials in a test sample. A first biological material has enzyme specificity for a first chromogenic substrate, a second biological material has enzyme specificity for a second chromogenic substrate, and a third biological material has specificity for one of the substrates. The chromogenic substrates form respective first and second colored water insoluble compounds upon reaction with specific enzymes. The first and second biological materials are capable of fermenting a sugar, and the third material does not ferment sugar. The test medium is adjusted to a pH conducive for color change of a pH indicator upon acidification due to fermentation, resulting in the formation of a zone of a third color around the water insoluble compounds of the sugar-fermenting materials. The sample is incubated, and examined for the presence of colonies of the first biological material, having the first color and an encircling zone of the third color; for colonies of the second material, having the second color and the encircling colored zone; for colonies of a third material having the first color, and not having the colored zone; and for colonies having neither color, with or without the colored zone, representing colonies of other biological materials.

36 Claims, No Drawings

TEST MEDIA AND QUANTITATIVE METHOD FOR IDENTIFICATION AND DIFFERENTIATION OF BIOLOGICAL MATERIALS IN A TEST SAMPLE

BACKGROUND OF THE INVENTION

The present invention relates to a method for the quantitative identification and differentiation of biological materials in a sample containing a plurality of different biological materials, and a test medium for use in the method.

The invention further relates to a quantitative method for detecting and identifying *Escherichia coli* 0157, with simultaneous quantitative detection and identification of other strains of *Escherichia coli* (*E. coli*), general coliforms and non-coliform Enterobacteriaceae in mixed microbial samples.

There has been an ongoing need to screen meat, dairy, water, and other food samples for the presence of offending substances such as bacteria, other microbes, and cells and tissues of other organisms. This need has taken on additional significance as a result of the discovery of the enteropathogenic *E. coli* 0157 in the early 1980s. Additional impetus was given by the public notoriety in more recent instances of disease and death from the ingestion of poorly cooked ground beef. As a result, much emphasis has been put into the development of test methods to determine the presence and quantities of such offending substances in biological materials such as food, dairy products, beverages and water, as well as in medical and veterinary test materials. This is important both to identify potential hazards in materials, and for diagnostic purposes.

In addition to the aforementioned need to determine the presence and quantities of *E. coli* 0157 in a test sample, there remains an ongoing need for faster and more reliable test methods to determine the presence in a test sample of many other biological materials which are known to affect the quality and safety of a product. A determination of the presence or absence of such biological materials provides an additional basis upon which the quality and safety of various substances may be evaluated.

The use of indicator organisms in biotechnology, diagnostic chemistry, microbiology, molecular biology and related fields as a basis upon which to determine product or test sample quality is well known. For example, the amount, or count, of *E. coli* or other coliforms present in water is considered a significant indicator of the cleanliness and safety of that water. Similarly, the presence of *E. coli* or other coliforms in food and dairy products is considered a significant indicator of the quality of these products. Also, quick and accurate identification of specific entities in medical test samples is important in the diagnosis of disease conditions. Improved test methods to effectively identify, separate and enumerate such bacterial types are needed, and there is a continuing search for faster, more accurate and more versatile test methods in this area.

Numerous test methods have been utilized to determine, identify and enumerate one or more indicator organisms. Some of these test methods only indicate the presence or absence of the microorganism, while others also attempt to quantify one or more of the particular organisms in the test sample. For example, a test referred to as the Presence/Absence (or P/A) test, may be utilized to determine the presence or absence of coliforms and *E. coli* in a test sample. A test medium comprising the β-galactosidase substrate O-nitrophenyl-β-D-galactopyranoside (ONPG), and the β-glucuronidase substrate 4-methyl-umbelliferyl-β-D-glucuronide (MUG), is inoculated with the test sample. To differentiate the general coliforms from *E. coli*, this test relies on the fact that generally all coliforms produce β-galactosidase, whereas only *E. coli* also produces β-glucuronidase in addition to β-galactosidase. If any coliforms are present (including *E. coli*), the broth medium turns a yellow color due to the activity of the galactosidase enzyme on the ONPG material, causing the release of a diffusible yellow pigment. If *E. coli* is present, the broth medium will demonstrate a blue fluorescence when irradiated with ultraviolet rays, due to the breakdown of the MUG reagent with the release of the fluorogenic dye caused by the production of the glucuronidase enzyme. These reactions are very specific, and allow the presence of both coliforms in general, as well as *E. coli* to be identified in a single sample. A disadvantage of this test is that it is not directly quantitative for either bacterial type, since both reagents produce diffusible pigments. The test also requires specific equipment for producing the ultraviolet rays. Further, this test may only be used to detect coliforms and *E. coli*. Other important microorganisms, such as the strain *E. coli* 0157 which is glucuronidase negative, are not detected, nor are other non-galactosidase-glucuronidase producing microorganisms.

The Violet Red Bile Agar (VRBA) method has been used to determine the quantity of both coliform and *E. coli* in a test sample. The test medium used in this method includes bile salts (to inhibit non-coliforms), lactose and the pH indicator neutral red. As coliforms (including *E. coli*) grow in the medium, the lactose is fermented with acid production, and the neutral red in the area of the bacterial colony becomes a brick red color. The results of this test are not always easy to interpret, and in order to determine the presence of *E. coli*, confirming follow-up tests, such as brilliant green lactose broth fermentation, growth in EC broth at 44.5° C. and streaking on Eosin Methylene Blue Agar (EMBA), must be performed.

The Membrane Filter (MF) method utilizes micropore filters through which samples are passed so that the bacteria are retained on the surface of the filter. This method is used most often when bacterial populations are very small, and a large sample is needed to get adequate numbers. The filter is then placed on the surface of a chosen medium, incubated, and the bacterial colonies growing on the membrane filter surface are counted and evaluated. This method is widely used and provides good results when combined with proper reagents and media. A disadvantage of this method is that it is expensive and time-consuming. It also does not work well with solid samples, or with samples having high counts of microorganisms. The MF method can be used in conjunction with the inventive method described in this application.

The reagent 5-bromo-4-chloro-3-indolyl-β-D-galactopyranoside (X-gal) is a known test compound for identifying coliforms. When acted on by the β-galactosidase enzyme produced by coliforms, X-gal forms an insoluble indigo blue precipitate. X-gal can be incorporated into a nutrient medium such as an agar plate, and if a sample containing coliforms is present, the coliforms will grow as indigo blue colonies. X-gal has the advantage over the compound ONPG, described above, in that it forms a water insoluble precipitate rather than a diffusible compound, thereby enabling a quantitative determination of coliforms to be made, when the test sample is incorporated into or onto a solidified medium.

A similar compound, 5-bromo-4-chloro-3-indolyl-β-D-glucuronide (X-gluc) is a known test compound for identifying *E. coli*. When acted on by the β-glucuronidase enzyme produced by most *E. coli*, X-gluc forms an insoluble indigo blue precipitate. X-gluc has the advantage over the compound MUG, described above, in that it forms a water insoluble precipitate, rather than a diffusible compound, thereby enabling a quantitative determination of *E. coli* to be made when the test sample is incorporated into or onto a solidified medium. Further, it does not require the use of ultraviolet light. X-gluc and its ability to identify *E. coli* are described in Watkins, et al, *Appl. Environ. Microbiol.* 54: 1874–1875 (1988). A similar compound, indoxyl-β-D-glucuronide, which also produces sharp blue colonies of *E. coli*, was described in Ley, et al, *Can. J. Microbiol.* 34: 690–693 (1987).

Although X-gal and X-gluc are each separately useful in the quantitative determination of either coliforms (X-gal) or *E. coli* (X-gluc), these indicator compounds have the disadvantage that they each contain the same chromogen. Therefore, they cannot be used together to identify and distinguish both *E. coli* and general coliforms in a single test with a single sample, since they both generate identically hued indigo blue colonies. A person using both reagents together would be able to quantitatively identify the total number of coliforms, the same as if X-gal was used alone, but would not be able to indicate which of the colonies were *E. coli* and which were other coliforms besides *E. coli*.

A recently developed test method for quantitatively identifying and differentiating general coliforms and *E. coli* in a test sample is described in U.S. Pat. No. 5,210,022, assigned to the assignee herein. This method improves upon prior art methods by allowing the quantitative identification of general coliforms and *E. coli* in a single sample. Additional confirmatory tests are not necessary. The test sample is added to a medium containing a β-galactosidase substrate, such as 6-chloroindolyl-β-D-galactoside, and a β-glucuronidase substrate, such as 5-bromo-4-chloro-3-indolyl-β-D-glucuronide (X-gluc). The β-galactosidase substrate is capable of forming a water insoluble precipitate of a first color upon reacting with β-galactosidase, and the β-glucuronidase substrate is capable of forming a water insoluble precipitate of a second color, contrasting with the first color, upon reacting with β-glucuronidase. As a result, general coliforms may be quantified by enumerating the colonies of the first color (having β-galactosidase activity), and *E. coli* may be quantified by enumerating the colonies of the second color (having both β-galactosidase and β-glucuronidase activity). Although the method described in the patent provides excellent results for the differentiation and identification of general coliforms and *E. coli*, it is unable to establish and quantify the presence of *E. coli* 0157 strains and non-coliform Enterobacteriaceae.

Other known methods to identify and differentiate certain microorganisms are based upon the differences exhibited by the microorganisms with regard to their ability to ferment certain carbohydrates, such as the sugar sorbitol. For example, general coliforms and most strains of *E. coli* are known to have the ability to ferment sorbitol. *E. coli* 0157 and most non-coliform Enterobacteriaceae do not ferment sorbitol. As a result, when a test sample is added to a fermentable medium containing sorbitol as the sole carbon source, such as MacConkey Sorbitol agar, in the presence of an appropriate pH indicator such as neutral red, the general coliforms and most *E. coli* strains grow as red colonies due to acid production from sorbitol fermentation. Non-sorbitol fermenters such as *E. coli* 0157 grow as colorless colonies on this medium. However, since there are also many non-sorbitol fermenting Enterobacteriaceae, it is virtually impossible to identify *E. coli* 0157 with any certainty on this medium. In addition, the test is incapable of distinguishing *E. coli* from general coliforms.

Therefore, a need exists to provide a test method that is effective for differentiating a wider variety of biological materials in samples containing mixed populations than may be accomplished with existing methods. Further, this need exists for methods that are faster, simpler and more versatile than prior methods.

SUMMARY OF THE INVENTION

The present invention overcomes the disadvantages of prior art methods by providing a test method for quantitatively identifying and differentiating biological materials in a test sample having a plurality of different biological materials, and a medium for use in the test method.

The present invention, in one form thereof, comprises a method for detecting the presence of and quantitatively identifying and differentiating specified biological materials in a test sample comprising a plurality of different biological materials, wherein a first biological material has enzyme specificity for a first chromogenic substrate, and a second biological material has enzyme specificity for a second chromogenic substrate, and wherein at least some of the biological materials are capable of fermenting a carbohydrate, such as a sugar. A test medium capable of forming a matrix or a solid surface with the test sample is provided. The test medium comprises a first chromogenic substrate, a second chromogenic substrate, a fermentable carbon source such as a specific sugar, a pH indicator and a nutrient base medium. The first chromogenic substrate is capable of forming a water insoluble compound of a first color upon reacting with an enzyme produced from or present in the first biological material, and the second chromogenic substrate is capable of forming a water insoluble compound of a color contrasting with the first color upon reacting with an enzyme produced from or present in the second biological material. The fermentable carbon source is capable of acidifying a portion of the medium upon fermentation by sugar-fermenting components of the test sample. The pH indicator causes a third color to be formed upon reaction to the acidification, which third color comprises a colored zone around the sugar-fermenting components and is visually distinguishable from the general background color of the medium. The nutrient base medium preferably comprises a solid, a gel or a solution for forming a solid. The pH of the test medium is adjusted to a range conducive for color change of the pH indicator upon acidification of the medium, and the test sample is thereafter inoculated into the test medium. The test medium containing the inoculated test sample is then incubated under conditions conducive for growth of colonies of the biological materials. The incubated test sample may then be examined for the presence of colonies having the first color, and having the third colored zone visibly discernable and distinguishable thereabout, which colonies represent sugar-fermenting colonies of the first biological material; for the presence of colonies having a second color and having the third colored zone visibly discernable and distinguishable thereabout, which colonies represent sugar-fermenting colonies of the second biological material; for the presence of colonies having the first color, and not having the second color or the third colored zone discernable and distinguishable therewith, such colonies representing colonies of a third biological material; for the presence of colonies not having either of said first and second colors, with or without the third colored zone, such colonies being colonies of at least a fourth biological material; and for the presence of colonies having a fourth color, with or without the third colored zone, such colonies being colonies of at least a fifth biological material. Each of the respective colonies is then enumerated to provide a count of each of the specified biological materials present in the test sample.

The present invention, in another form thereof, comprises a method for detecting the presence of and quantitatively identifying and differentiating E. coli 0157, other E. coli strains not including E. coli 0157, general coliforms and non-coliform Enterobacteriaceae in a test sample. A test medium capable of forming a matrix or a solid surface with the test sample is provided. The test medium comprises a chromogenic β-galactosidase substrate capable of forming a water insoluble compound of a first color upon reacting with β-galactosidase, a chromogenic β-glucuronidase substrate capable of forming a second water insoluble component of a color visibly contrasting with the first color upon reacting with β-glucuronidase, sorbitol as the sole fermentable carbon source, a pH indicator for causing a third color to be formed upon acidification resulting from sorbitol fermentation, the third color comprising a colored zone around the sorbitol-fermenting components which contrasts with the normal background color of the medium, and a nutrient base medium. The pH of the test medium is adjusted to a range conducive for color change of the pH indicator upon acidification of the medium, and the sample is thereafter inoculated into the test medium. The test medium containing the sample is incubated under conditions conducive for growth of general coliforms, E. coli, E. coli 0157 and non-coliform Enterobacteriaceae, to thereby produce first and second colored precipitates corresponding to said colonies, and to produce a zone of the third color around the sorbitol-fermenting components. The test medium may then be examined for the presence of colonies having the first color and the third colored zone visibly discernable and distinguishable thereabout, these colonies being colonies of general coliforms having β-galactosidase activity but not β-glucuronidase activity, and being sorbitol fermenters; for the presence of colonies having a second color and the third colored zone visibly discernable and distinguishable thereabout, such colonies being colonies of E. coli having β-glucuronidase activity and β-galactosidase activity, and being sorbitol fermenters; for the presence of colonies having the first color, and not having the second color or the third colored zone discernable and distinguishable therewith, such colonies being colonies of E. coli 0157 having β-galactosidase activity but not β-glucuronidase activity, and being sorbitol non-fermenters; for the presence of colonies not having either of the first and second colors, with or without the third colored zone, such colonies being non-coliform Enterobacteriaceae having neither β-galactosidase activity nor β-glucuronidase activity, with or without the ability to ferment sorbitol; and for the presence of colonies having a fourth color, with or without the third colored zone, such colonies representing certain strains of some genera such as Salmonella or Shigella not having β-galactosidase activity but having β-glucuronidase activity, with or without the ability to ferment sorbitol. Each of the colonies may then be enumerated to provide a count of each of the selected microorganisms. Alternatively, only the particular colonies of interest in the particular test sample need be enumerated.

The present invention, in yet another form thereof, comprises a test medium for detecting the presence of biological materials in a test sample. The test medium comprises a first chromogenic substrate, a second chromogenic substrate, a fermentable carbon source such as a sugar, a pH indicator and a nutrient base medium. The first chromogenic substrate is capable of forming a water insoluble compound of a first color upon reacting with an enzyme from said first biological material, and the second chromogenic substrate is capable of forming a water insoluble compound of a second color contrasting with the first color upon reacting with an enzyme from the second biological material. The fermentable carbon source is capable of acidifying a portion of the medium upon fermentation by sugar-fermenting components of the test sample. The pH indicator causes a third color to be formed upon reaction to the acidification, which third color comprises a colored zone around the sugar-fermenting components. The nutrient base medium may comprise a solid, a gel or a solution for forming a solid.

The method and media of the present invention allow the simultaneous growth, isolation, quantification and identification of biological substances, such as general E. coli strains, E. coli 0157, other coliforms and non-coliform members of the Enterobacteriaceae family from a sample incorporated into the test medium in a single petri plate. No pre-enrichment of the sample is required, although pre-enrichment may be utilized if desired. The test results are available within 24–48 hours, and the test essentially comprises the mere addition of the test sample to the medium in the plate, the incubation of the test medium and the enumeration of the respective colonies in the test sample. Most other tests require more steps, and generally require a longer period of time in which to obtain the test results. In addition, the inventive method is not dependent upon one carefully controlled incubation temperature.

DETAILED DESCRIPTION OF THE INVENTION

The method and medium of the present invention allow the simultaneous quantitative identification and differentiation of a variety of selected biological materials in a sample of mixed populations of biological materials.

The inventive method and medium are particularly useful for the quantitative identification and differentiation of E. coli 0157 in mixed microbial samples, with the simultaneous quantitative identification and differentiation of other strains of E. coli, general coliforms, and non-coliform Enterobacteriaceae.

Microorganisms having β-galactosidase activity include those commonly known by the designation "coliform." There are various definitions of "coliform," but the generally accepted ones include bacteria which are members of the Enterobacteriaceae family, and have the ability to ferment the sugar lactose, with the evolution of gas and acids.

Microorganisms having β-glucuronidase activity in addition to β-galactosidase activity primarily include most strains of coliform of the species E. coli, with the exception of E. coli 0157. E. coli 0157 is one of about 3% of E. coli strains that exhibit β-galactosidase activity but do not exhibit β-glucuronidase activity.

The term "general coliforms" as used in this application refers to coliforms other than the various strains of E. coli. These "general coliforms" are gram-negative, non-sporeforming microorganisms having β-galactosidase activity (i.e., lactose fermenters), but not having β-glucuronidase activity, and having the ability to ferment the sugar sorbitol.

The term "non-coliform Enterobacteriaceae" as used in this application refers to microorganisms of the family Enterobacteriaceae not having β-galactosidase activity.

The term "β-galactosidase substrate" as used herein refers to a β-galactoside comprising galactose joined by a β-linkage to a substituent that forms an insoluble colored precipitate when liberated by the action of β-galactosidase on the substrate.

The term "β-glucuronidase substrate" as used herein refers to a β-glucuronide comprising glucuronic acid joined by a β-linkage to a substituent that forms an insoluble colored precipitate when liberated by the action of β-glucuronidase on the substrate.

The β-galactosidase substrates and compounds described herein as "galactosides," as well as the β-glucuronidase substrates and compounds described herein as "glucuronides," each may comprise carboxylate salts formed by reacting a suitable base with the appropriate galactosidase or glucuronic carboxyl group. Suitable bases include alkali metal or alkaline earth metal hydroxides or carbonates, for example, sodium hydroxide, potassium hydroxide, calcium hydroxide, magnesium hydroxide, and corresponding carbonates; and nitrogen bases such as ammonia, and alkylamines such as trimethylamine, triethylamine and cyclohexylamine.

The method of the present invention is designed to take advantage of distinguishing characteristics found in certain microorganisms, so that the microorganisms may be quantitatively identified and differentiated from each other. The method is particularly suitable for the quantitative identification and differentiation of the different classes of microorganisms described previously, i.e., general coliforms, *E. coli*, *E. coli* O157 and non-coliform Enterobacteriaceae. Although the inventive method is particularly suitable for the microorganisms described above, it is not limited to the quantitative identification and differentiation of those particular microorganisms, as the techniques have application to the quantitative identification and differentiation of a wide variety of biological materials.

The separation and identification of *E. coli* O157 from other strains of *E. coli* has been particularly problematic, as all *E. coli* strains share many common characteristics. However, there are three primary differences which provide a basis upon which to distinguish *E. coli* O157 from the other *E. coli* strains. These are the unthrifty growth of *E. coli* O157 at temperatures above 42° C., the inability of *E. coli* O157 to produce the enzyme glucuronidase, and the inability of *E. coli* O157 to ferment the sugar sorbitol. Although these differences provide a general backdrop for use in identifying and separating the two *E. coli* types, additional factors complicate this identification and separation.

In mixed populations of microorganisms found in nature, such as those including both *E. coli* and *E. coli* O157, many other closely related organisms are also normally present. Many of these microorganisms are capable of living and metabolizing under the same or similar conditions as the *E. coli* strains. Most of the closely related organisms are members of the family Enterobacteriaceae, as are all species of *E. coli*. The Enterobacteriaceae are gram-negative, non-sporeforming, rod-shaped bacteria. Some of the most well known genera are Citrobacter, Edwardsleila, Enterobacter, Escherichia, Klebsiella, Proteus, Salmonella, Shigella and Yersinia. Within this family are those genera which are commonly designated the coliform bacteria. Coliform bacteria retain the general generic characteristics, but in addition produce the enzyme galactosidase, which is instrumental in the fermentation of the sugar lactose. The coliform genus Escherichia also produces the enzyme galactosidase, and in addition, most strains of this genus also produce the enzyme glucuronidase. However, the strain *E. coli* O157 is one of only about 3% of *Escherichia coli* strains that do not have the ability to produce glucuronidase.

Due to the characteristic similarities of these closely related bacteria, it has proven difficult to identify and separate *E. coli* O157 from other members of the Enterobacteriaceae family. As a result, easy to read and formulate test media to accomplish this identification and separation have not been available, and it has generally been necessary to go to complex and expensive methods utilizing antigen-antibody matching or DNA probes to determine the presence of the *E. coli* O157 in mixed microbial populations. Such techniques are not only expensive and time-consuming, but often give false positive or false negative results.

The method described in U.S. Pat. No. 5,210,022, incorporated herein by reference, allows the quantitative identification and differentiation of general coliforms and *E. coli*. The differentiation of these two microorganisms is based upon the characteristic ability of general coliforms to produce galactosidase, and thereby form a water insoluble precipitate of a first color upon reaction with a β-galactoside, and the characteristic ability of *E. coli* to produce glucuronidase in addition to galactosidase, and thereby form a water insoluble precipitate of a color contrasting with the first color upon reaction with a β-glucuronide.

The present invention goes beyond the method taught in U.S. Pat. No. 5,210,022. With the inventive method, a quantitative identification and differentiation may be made of not only general coliforms and *E. coli*, as in the patent, but also of the enteropathogenic *E. coli* O157 as well as various species of non-coliform Enterobacteriaceae. Sorbitol and a suitable pH indicator are incorporated into a test medium with the chromogenic agents. Since one of the differences between *E. coli* O157 and other *E. coli* is the inability of *E. coli* O157 to metabolize the sugar sorbitol, the use of sorbitol in the test medium provides a means to distinguish these two *E. coli* strains. The chromogenic agents are selected to provide a basis for a quantitative differentiation of coliforms having β-galactosidase activity from those strains of *E. coli* having β-galactosidase activity in addition to β-glucuronidase activity. The inclusion of sorbitol and the pH indicator in the medium does not affect this quantitative differentiation of coliforms from *E. coli*, but additionally allows the quantitative detection and differentiation of *E. coli* O157 and non-coliform Enterobacteriaceae from general coliforms and most other *E. coli*. *E. coli* O157 may be distinguished from the non-coliform Enterobacteriaceae due to the β-galactosidase activity of *E. coli* O157, which activity is not present in the non-coliform Enterobacteriaceae.

The specific β-galactosidase substrate (β-galactoside) and the specific β-glucuronidase substrate (β-glucuronide) for use in the test medium are selected so that the precipitates formed by each of the substrates are of contrasting colors, thereby providing a means to distinguish general coliforms from *E. coli*. As a result, colonies of microorganisms having β-galactosidase activity but not β-glucuronidase activity, and colonies of microorganisms having either β-glucuronidase activity alone, or both β-galactosidase and β-glucuronidase activity, can be visually distinguished. The exact color of each type of microorganism colony is not crucial as long as each type can be distinguished. The precipitates should be insoluble in the test medium so that the colonies of microorganisms producing each precipitate can be visually counted. Further, the β-galactoside and β-glucuronide should be compounds that are approximately colorless or are not deeply colored, so that they do not interfere with the detection of the colored insoluble precipitates produced by the action of β-galactosidase and β-glucuronidase. The β-galactosides and β-glucuronides should be compounds that can be made soluble in the test medium.

The determination of whether a given β-galactoside or β-glucuronide is operable in the test medium can be made by a simple test. The β-galactoside or β-glucuronide is incorporated in a solid test medium which is then inoculated with general coliforms or *E. coli*. If colored colonies grow in the test medium, the particular β-galactoside or β-glucuronide may be used, subject to the following test. The determination of whether a given β-galactoside and β-glucuronide can be used together can be made by incorporating the two compounds together in a solid medium which is then inoculated with a mixture of both general coliforms and *E. coli*, and incubated at a suitable temperature. If the colonies of *E. coli* and the colonies of general coliforms can be visually differentiated by a contrast in color of each type of colony, then the particular combination of β-galactoside and β-glucuronide is suitable.

A suitable chromogenic compound for the practice of the method of this invention is 5-bromo-4-chloro-3-indolyl-β-D-galactopyranoside (X-gal). X-gal is a commercially available β-galactosidase substrate that produces an insoluble precipitate having an approximately indigo blue color when reacted upon by β-galactosidase. Permissible β-glucuronides that can be used with X-gal include compounds that produce an insoluble precipitate having a color such as red or yellow that contrasts with indigo blue and is not totally masked by the indigo blue color. One such example is the compound 6-chloroindolyl-β-D-glucuronide. This compound produces an insoluble precipitate having a magenta color contrasting with and visually distinguishable from indigo blue. The preparation of this compound and other suitable compounds for use herein is described in the aforementioned incorporated by reference U.S. Pat. No. 5,210,022.

Another suitable chromogenic compound for the practice of the method is 5-bromo-4-chloro-3-indolyl-β-D-glucuronide (X-gluc). X-gluc is a commercially available β-glucuronide that produces an insoluble precipitate having an approximately indigo blue color when reacted upon by β-glucuronidase. Indoxyl-β-D-glucuronide is a similar compound, the preparation of which is described in the aforementioned article by Ley et al., in *Can J. Microbiol.*, the disclosure of which is incorporated by reference. Permissible β-galactosides that can be used with X-gluc or indoxyl-β-D-glucuronide include substrates that produce an insoluble precipitate having a color such as red or yellow that contrasts with indigo blue. An example of a suitable β-galactoside is the compound 6-chloroindolyl-β-D-galactoside. This compound produces an insoluble precipitate having a magenta color contrasting with and visually distinguishable from indigo blue. The preparation of this compound is described in the aforementioned U.S. Pat. No. 5,210,022. Other suitable chromogenic compounds are also specified in the patent.

It is preferred that the β-galactoside and the β-glucuronide are selected so that the β-glucuronide produces an insoluble precipitate that is darker in color than the insoluble precipitate produced by the β-galactoside. This allows the precipitate produced by the β-glucuronide to mask the precipitate produced by the β-galactoside in colonies of *E. coli*, and makes it easier for colonies of *E. coli* to be differentiated from colonies of general coliforms. Alternatively, the precipitate produced by the β-galactoside may be masked by using more of the β-glucuronide and less of the β-galactoside. In a preferred embodiment, 6-chloro-3-indolyl galactoside is used as the β-galactoside and 5-bromo-4-chloro-3-indolyl glucuronide is used as the β-glucuronide. When these substrates are used in the medium, coliforms are identified by the presence of red colonies formed due to the presence of the enzyme galactosidase. *E. coli* is identified by the formation of purple (red+blue) colonies, formed due to the presence of both galactosidase (which produces red colonies) and glucuronidase (which produces blue colonies) in these strains of *E. coli*.

Other β-galactosides and β-glucuronides that may be utilized include those that fall into the general category of substituted indolyl β-galactosides and β-glucuronides. While it is not intended to limit the invention to any particular theory or mechanism, it is believed that when β-galactosidase and β-glucuronidase substrates having substituted indolyl substituents are reacted upon by their respective enzymes, the substituted indolyl substituents released by action of the enzyme convert in situ to insoluble indigo analogs. For example, when 6-chloroindolyl-β-D-galactoside is acted upon by β-galactosidase, the released 6-chloroindolyl reacts with itself and forms 6,6'-dichloroindigo, a magenta-colored precipitate. This suggests that other compounds similar to 6-chloroindolyl-β-D-galactoside or 6-chloroindolyl-β-D-glucuronide could be made and utilized based upon symmetrical indigo analogs having a color similar to 6,6'-dichloroindigo. The synthesis and absorption spectra of symmetrical chloroindigos were reported by Sadler et al., *JACS* 78, 1251–1255 (1956), the disclosure of which is incorporated herein by reference. It appears therein that the compounds 4,4',6,6'tetrachloroindigo, 6,6',7,7'tetrachloroindigo, and 4,4',6,6', 7,7'hexachloroindigo are similar in color to 6,6'-dichloroindigo. Thus, the respective β-galactosides, namely 4,6-dichloroindolyl-β-D-galactoside, 6,7-dichloroindolyl-β-D-galactoside and 4,6,7-trichloroindolyl-β-D-galactoside, and salts thereof, could be made and used as β-galactosidase substrates in the same manner as 6-chloroindolyl-β-D-galactoside. Other galactosidase substrates suitable for use in the invention to form reddish-colored precipitates include 5-bromo-6-chloro-3-indolyl-β-D-galactoside and 6-chloro-3-indolyl-β-D-galactoside. It has additionally been found that certain naphthyl substituted galactosides, such as 2-naphthyl-β-D-galactoside, may also be utilized as galactosidase substrates, since these naphthyl-substituted compounds form a red precipitate under the conditions specified in the inventive method.

Similarly, the respective β-glucuronides, namely 4,6-dichloroindolyl-β-D-glucuronide, 6,7-dichloroindolyl-β-D-glucuronide and 4,6,7-trichloroindolyl-β-D-glucuronide, and salts thereof, as well as naphthyl-substituted glucuronides such as naphthol-AS-BA-β-D-glucuronide, could be made and used as β-glucuronidase substrates in the same manner as 6-chloroindolyl-β-D-glucuronide. Other suitable glucuronidase substrates that form reddish-colored precipitates include 5-bromo-6-chloro-3-indolyl-β-D-glucuronide and 6-chloro-3-indolyl-β-D-glucuronide. However, in practice, the above-listed glucuronides would not be used with the listed galactosides because the colored precipitates formed by each of the respective substrates would not be readily distinguishable, since they each contain the same chromogen. Rather, in such instances wherein a reddish precipitate is formed by the galactosidase substrate, glucuronides such as 5-bromo-4-chloro-3-indolyl-β-D-glucuronide, indoxyl-β-D-glucuronide, 4-chloro-3-indolyl-β-D-glucuronide, 5-bromo-3-indolyl-β-D-glucuronide and N-methyl-3-indolyl-β-D-glucuronide, and their salts, may be utilized, since the precipitates formed by these substrates are of a color (generally blue or green) that contrasts with the color formed by these galactosides (generally a reddish color).

Similarly, if the glucuronides specified above that form a reddish-colored precipitate are utilized, the galactosides selected would be those that form precipitates having a color distinguishable from the color of the precipitates formed by the glucuronidase substrate. In this event, suitable galactosides would include 5-bromo-4-chloro-3-indolyl-β-D-galactoside, 4-chloro-3-indolyl-β-D-galactoside, 5-bromo-3-indolyl-β-D-glucuronide and N-methyl-3-indolyl-β-D-galactoside, and their salts. Most of the above-listed compounds, or their salts, may be obtained from commercial sources such as Inalco Pharmaceuticals, Inc., of Horsham, Pa., and Diagnostic Chemicals Limited, of Oxford, Conn.

A suitable carbon source and an appropriate pH indicator are also incorporated into the test medium. In the preferred embodiment the sugar sorbitol is utilized as the carbon source to enable the differentiation of sorbitol-fermenting microorganisms, such as general coliforms and E. coli, from non-sorbitol fermenters, such as E. coli 0157 and some non-coliform Enterobacteriaceae. Although sorbitol is utilized in the preferred embodiment, other sources of carbon such as complex carbohydrates, other sugars, proteins and long chain lipids may also be used under appropriate conditions and with appropriate pH indicators to react biochemically with substrates to produce organic acids, and therefore also fall within the scope of the present invention.

The pH indicator causes a colored zone to be created around those colonies which ferment sorbitol with the production of acid. No zone is created around those colonies that do not ferment sorbitol. The pH of the final medium is critical to the effectiveness of this method, as the pH must be such that the pH indicator turns the medium the desired color. Although various pH indicators may be used, phenol red is the preferred indicator when the method is utilized to identify and differentiate E. coli 0157 from the microorganisms specified above. When phenol red is used as the pH indicator, the pH should be adjusted within the range of about 7.0 to 7.6, and preferably about 7.2. With the use of phenol red at this pH, a yellow zone is created around the sorbitol fermenters due to the production of acid upon fermentation. The area around the non-sorbitol fermenters remains colorless, or in some cases red due to a small amount of color leakage from precipitates formed due to the presence of galactosidase. Other indicators such as Brom Thymol Blue (BTB) have also been used to detect and distinguish E. coli 0157 from E. coli. When other pH indicators are utilized, the reaction conditions must be adjusted to the appropriate pH for the particular indicator chosen. In addition, when selecting a pH indicator, it is important to select an indicator that produces colors upon acidification or alkalinization that are distinguishable from the colors of the particular chromogens used in the test medium.

It is important to control the amount of the sugar incorporated in the medium. For example, too high a concentration of sorbitol will result in excessive acid production. In such event, a relatively small number of acid producing colonies may cause the medium in the entire petri plate to turn yellow, and thereby mask the non-sorbitol using colonies. Preferably, the amount of sorbitol should be between about 2 and 7 grams per liter of medium, most preferably about 5 g/l.

In addition, for best results, an overlay of medium should be placed over the sample to lock the bacteria into the matrix of the medium. Since colonies growing on an air exposed surface of a medium may not respond in exactly the same way as those embedded in the medium, the addition of an overlay of medium provides more consistent and accurate test results.

Preparation of Test Medium

The preparation of a test medium for use in the quantitative identification and differentiation of E. coli 0157, with simultaneous quantitative detection and identification of E. coli, general coliforms and non-coliform Enterobacteriaceae in mixed microbial samples will be described.

The test medium is formed by combining the selected chromogens, i.e., the β-galactoside and the β-glucuronide, sorbitol and the pH indicator with a nutrient base medium. Sorbitol is the only sugar added to the medium, as the test method depends upon the fermentation or nonfermentation of sorbitol as one of the differentiation processes. When phenol red is used as the pH indicator, this indicator is red at neutral or alkaline conditions, and yellow in acidic conditions created upon fermentation of sorbitol. In a preferred embodiment, bile salts are also added to the medium to inhibit the growth of many bacteria other than members of the Enterobacteriaceae, thus making the test more selective.

The nutrient base medium may be any one of many culture medium formulations known in the art for growing microorganisms. Generally such media include growth nutrients, buffers, water, and a gelling agent. Possible gelling agents include agars, pectins, carrageenans, alginates, locust bean, xanthins, guars and gellens, among others.

The following example describes the preparation of a test medium suitable for use in the present invention. The amounts of the respective ingredients listed are per liter of test medium:

| | |
|---|---|
| peptone (casein digest) | 10 g |
| yeast extract | 5 g |
| sodium chloride | 3 g |
| bile salts | 1 g |
| sorbitol | 5 g |
| phenol red | 25 mg |
| 5-bromo-4-chloro-3-indolyl glucuronide | 75 mg |
| 6-chloro-3-indolyl galactoside | 150 mg |
| bacteriological quality agar | 17 g |

The above ingredients are blended in about one liter of deionized water heated to 90°–100° C. The pH of the solution is then adjusted to about 7.2 with NaOH or tartaric acid (10% solutions). The medium is sterilized at 121° C. and 15 pounds pressure for 15 minutes, cooled to 45° C., and poured into sterile Petri plates (20 mL/plate) for use.

A pectin-based test medium may be prepared using the same steps described above except that 25 gm of low methoxyl pectin is used as the solidifying agent in place of the agar gum. This medium is poured at room temperature into petri plates containing a thin gel layer containing calcium ions, which combine with the pectin to form a solid gel. A suitable pectin culture medium is described in U.S. Pat. No. 4,241,186 and U.S. Pat. No. 4,282,317, the disclosures of which are incorporated herein by reference. A pectin-based medium is preferred over a standard agar medium because it has the advantages of convenience and temperature independence for the user. The use of pectin media has been well described in the literature, and has been accepted as a result of AOAC collaborative studies, as well as other published and in-house investigations. A suitable pectin medium for use in the inventive method is commercially available from RCR Scientific, Inc., of Goshen, Ind.

Although the method has been described as utilizing a solid pectin or agar medium in its preferred embodiment, the medium need not necessarily be in solid form. For example, an absorbent pad may be placed in a petri dish, and a liquid medium containing all of the necessary nutrients and reagents previously described is added in a manner such that it is absorbed by the pad. The absorbent pad provides a solid surface upon which the microorganisms can grow as discrete colony-forming units similar to those that develop on a medium solidified with agar or other solidifying agents.

Inoculation of the Test Medium with the Sample

The test medium may be inoculated with the sample to be tested by any method known in the art for inoculating a medium with a sample containing microorganisms. For example, the sample to be tested may be added to the petri plates prior to adding the medium, or the sample may be added to the unsolidified medium prior to pouring in the plates (pour plate technique). When the pour plate technique is utilized, an overlay layer is added after the medium has solidified in the plate. Alternatively, the test sample may be spread on the surface of the plates after the plates have cooled and solidified, and then covered with an overlay layer (swab or streak plate technique).

The inventive method may also be used in combination with the Membrane Filter (MF) method described above. In this method, the sample, which in most cases comprises an aqueous solution containing the biological material to be identified, is filtered through a micropore filter so that the biological materials are captured on the surface of the filter. The filter is then placed in a petri dish on the surface of the medium for incubation, to enable the biological materials on the surface to grow into visible colonies. The medium in the petri dish may be presolidified agar or pectin based medium, or alternatively, may be an absorbent pad soaked with liquid medium containing the necessary nutrients and reagents. This latter approach allows the inventive methods to be used without a separate solidifying agent in the medium, but still provides a hard surface for the biological materials to develop on so that they can grow as distinct, discrete colony-forming units similar to those that develop on a medium solidified with agar or other agents.

Incubation of the Test Medium

The inoculated test medium is incubated for a sufficient period of time and at a temperature sufficient to enable the individual microorganisms present in the sample to grow into detectable colonies. Suitable incubation conditions for growing microorganisms in a medium are well known in the art. Preferably, in the quantitative identification and differentiation of *E. coli* 0157 as described, the test medium is incubated for about 24–48 hours at a temperature of about 300°–40° C.

If desired, the selectivity of the method may be further improved by controlling the incubation temperature at 42° C., rather than between 300°–40° C. *E. coli* (including the strain 0157) grows well at 42° C., however, this temperature is inhibitory to the growth of many other related microbes. Utilizing this higher temperature may provide improved results for certain microorganisms by improving the selectivity, but at the same time will diminish the overall versatility of the general medium, since it does not give an accurate indication of the presence of certain other microbial types.

Unless inhibitors of the general microbial population are used, the general microbial population, (in addition to the non-coliform Enterobacteriaceae, general coliforms, *E. coli* and *E. coli* 0157) will also grow in the incubated test medium. Because microorganisms other than general coliforms and the various *E. coli* strains rarely produce β-galactosidase or β-glucuronidase, most of the general microbial population will normally show on a standard agar pour plate as white or colorless colonies.

Examination of the Test Medium and Enumeration of Microorganisms

General coliforms produce β-galactosidase, which acts upon the β-galactoside in the test medium, causing the β-galactoside to form an insoluble precipitate having a color in accordance with the particular β-galactoside used. Because the precipitate formed is insoluble in the test medium, it remains in the immediate vicinity of the β-galactosidase-producing microorganisms. As these microorganisms reproduce to form colonies, the colonies have the color produced by the β-galactoside.

Since most strains of *E. coli* also produce β-galactosidase and β-glucuronidase, insoluble precipitates of both the β-galactoside and β-glucuronide are formed by the action of the respective enzymes. The colonies of *E. coli* show as colonies having a color different from and contrasting with the color of the colonies of general coliforms, due to the presence of the contrastingly colored insoluble precipitate of the β-glucuronide. *E. coli* 0157, since it is one of the 3% of strains of *E. coli* that is glucuronidase negative, reacts in the same manner as the general coliforms and causes the formation of an insoluble precipitate having the same color as the precipitate formed by the general coliforms.

The colonies of those microorganisms that are sorbitol fermenters are further modified as a result of the acid produced from the sorbitol fermentation. A zone is created around these sorbitol-fermenting colonies, which zone is colored in accordance with the particular pH indicator utilized and the pH of the reaction medium. No zone is created around colonies that do not ferment sorbitol, such as *E. coli* 0157.

Since the specific chromogens, namely the β-galactoside and the β-glucuronide, and the specific pH indicator are selected so that the colors resulting from the incubation provide a visible contrast, the colonies of each type of microorganism present can be visually differentiated. Thus, for example, if 6-chloro-3-indolyl galactoside is used as the β-galactoside, 5-bromo-4-chloro-3-indolyl glucuronide is used as the β-glucuronide, and phenol red is used as the pH indicator in the test medium, *E. coli* 0157 colonies appear in the incubated medium as red colonies (CFU) surrounded by a noticeably reddish haze around the colony. The reddish haze around these colonies is caused by a small amount of enzyme leakage into the medium surrounding the colony, which leakage produces a slightly colored red "halo" around the colony, and is not formed as a result of a color change of the pH indicator. Other *E. coli* colonies appear as purple (resulting from the combination of red and blue colonies) colonies (CFU) surrounded by a yellow zone, which yellow zone is formed due to the reaction of the pH indicator to the acid produced upon fermentation. General coliforms appear as red colonies (CFU) surrounded by a yellow zone. Some non-coliform Enterobacteriaceae such as most Salmonella strains appear as colorless or white colonies (CFU) surrounded by a yellow zone, since most Salmonella ferment sorbitol with acid production, but do not produce either galactosidase or glucuronidase. Certain strains of some genera such as Salmonella or Shigella grow as light blue colonies due to glucuronidase (but not galactosidase) production. Other Enterobacteriaceae such as Proteus appear as colorless colonies without any zone surrounding these colonies, due to the lack of either enzyme production or acid fermentation of the sorbitol.

The colonies of each type of microorganism may then be enumerated by counting the colonies of each color combination, or by other methods known in the art for enumerating microorganisms on a test plate. The number of colonies of each type indicates the number of microorganisms of each type originally present in the sample before incubation. The versatility of the inventive method enables the quantitative identification and differentiation of as many of the biological materials as may be of interest in the particular test sample. For example, if only general coliforms, E. coli and E. coli 0157 are of interest in a particular sample, the colonies representing these bacteria may be enumerated, and in this event it is not necessary to also enumerate the colonies of other biological materials, such as Salmonella, Shigella and Proteus.

Thus, it will be appreciated that the invention as described may be used to quantitatively identify and differentiate multiple types of microorganisms in a single test sample simply by distinguishing various color combinations formed as a result of controlled reactions involving said microorganisms.

Optional Ingredients

The method of the present invention does not require inhibitors. However, as stated, the medium may be made more selective when used for the identification and differentiation of biological materials such as general coliforms, E. coli and E. coli 0157 by the addition of various compounds that are known to be inhibitory to the general microbial population, but have little or no effect on coliforms. For example, substances such as bile, sodium lauryl sulfate, desoxycholates and/or polyglycol ethers may be incorporated into the medium to inhibit the growth of bacteria not of interest to the particular test. Suggested concentrations of these compounds per liter of medium are: a) bile salts, about 1.0 g/liter, b) sodium lauryl sulfate, about 0.2 g/liter, c) sodium desoxycholate, about 0.2 g/liter, d) polyglycol ether, about 0.1 ml/liter. The addition of one or more of these compounds may reduce the background (non-Engerobacteriaceae) microorganisms present, thereby making a less cluttered plate, and may reduce the possibility of inhibition or interference by the non-Enterobacteriaceae organisms in the sample. It is also possible to eliminate the presence of some non-E. coli Enterobacteriaceae and/or coliforms by the addition of chemicals such as acriflavine, and/or antibiotics such as cefsulodin, cefoxime, novobiocin and similar inhibitory compounds known in the art. However, as with the inhibitors above, this approach reduces the ability of the medium to screen for and quantify those microorganisms inhibited or eliminated by these materials.

It is also possible to enhance the enzyme production of the general coliforms by the addition to the medium formulations of very small amounts of enzyme inducers. For example, a specific inducer for β-galactosidase is commercially available and is known chemically as isopropyl-β-D-thiogalactopyranoside (IPTG). Adding approximately 150 mg IPTG per liter of medium has a positive and noticeable effect on the speed of enzyme production for some species of coliforms.

EXAMPLE

Test plates were prepared containing the ingredients listed in the formula provided above, but with pectin substituted for agar as the gelling agent. The medium was inoculated with the respective bacteria as indicated in the following Table.

The Table describes the manner in which E. coli 0157, general coliforms, E. coli and the non-coliform Enterobacteriaceae, Proteus and Salmonella, may be distinguished when using the test medium described in the example above. As shown in the Table, when the inventive test medium is used in a test for the identification or differentiation of E. Coli 0157 in a sample containing general coliforms, or the E. coli and the non-coliform Enterobacteriaceae, Proteus and Salmonella, visual distinctions may be recognized for each of the specific colonies of the respective microorganisms. The versatility of the inventive method is not possible with the other test media described in the Table.

| | COMPARATIVE MEDIA | | | | | |
|---|---|---|---|---|---|---|
| Media No. | (1) | (2) | (3) | (4) | (5) | (6) |
| EC0157 | red red haze | red red zone | white no zone | white | blue | white |
| Other E. coli (most) | purple yellow zone | red yellow zone | blue yellow zone | red | blue | blue |
| Coliforms (most) | red yellow zone | red yellow zone | white yellow zone | red | blue | white |
| Proteus (most) | white no zone | white no zone | white no zone | white | white | white |
| Salmonella (most) | white yellow zone | white yellow zone | white yellow zone | white or red | white or red | white or red |

(1) Media formula provided above.
(2) Media formula provided above, less 5-bromo-4-chloro-3-indolyl glucuronide.
(3) Media formula provided above, less 6-chloro-3-indolyl galactoside.
(4) MacConkey sorbitol-standard formulation.
(5) MacConkey sorbitol plus 5-bromo-4-chloro-3-indolyl galactoside.
(6) MacConkey sorbitol plus 5-bromo-4-chloro-3-indolyl glucuronide.

While this invention has been primarily described in terms of its preferred embodiment, one skilled in the art will appreciate that the present invention can be further modified within the spirit and scope of this disclosure to enable the identification and differentiation of other biological materials present in samples of mixed populations. This application is therefore intended to cover any variations, uses, or adaptations of the invention using its general principles. For example, the inventive technique may be used to quantitatively identify and differentiate any of a wide variety of biological materials, as long as those biological materials exhibit differences in enzyme specificity, and at least some of the biological materials exhibit differences in their respective abilities to ferment various carbohydrates at a selected pH in the presence of a suitable pH indicator for use at the pH. In the practice of the present invention, one need only determine that the particular chromogens to be utilized for the visual differentiation produce distinguishable colors upon reaction with the respective enzymes, and select an appropriate carbohydrate and pH indicator such that yet another visually distinguishable color is produced upon fermentation of the carbohydrate under the appropriate reaction conditions for the pH indicator.

In addition to the foregoing, this application is intended to cover such departures from the present disclosure as come within known or customary practice in the art to which this invention pertains and which fall within the limits of the appended claims.

What is claimed is:

1. A method for quantitatively identifying and differentiating specified biological materials in a test sample comprising a plurality of different biological materials, wherein a first one of said biological materials has enzyme specificity for a first chromogenic substrate, and a second one of said biological materials has enzyme specificity for a second chromogenic substrate, and wherein at least some of said biological materials in said test sample are capable of fermenting a carbohydrate, said method comprising the steps of:

providing a test medium capable of forming a matrix or a solid surface with said test sample, said test medium comprising said first chromogenic substrate and said second chromogenic substrate, said first chromogenic substrate capable of forming a water insoluble compound of a first color upon reacting with an enzyme from said first biological material, and said second chromogenic substrate capable of forming a water insoluble compound of a color contrasting with said first color upon reacting with an enzyme from said second biological material; a fermentable component capable of acidifying a portion of the medium upon fermentation, said component comprising a carbohydrate, and said fermentation caused by carbohydrate-fermenting components of said test sample; a pH indicator for causing a third color to be formed upon reaction to said acidification, said third color comprising a colored zone around said carbohydrate-fermenting components; and a nutrient base medium;

adjusting the pH of said test medium to a range conducive for color change of the pH indicator upon acidification of said portion of the medium;

inoculating said test medium with said test sample;

incubating said test medium under conditions conducive for growth of colonies or activity of said biological materials, to thereby produce said contrasting colored water insoluble compounds;

examining said test medium for the presence of colonies having said first color, and having said third colored zone discernable and distinguishable thereabout, said colonies being colonies of said first biological material, and being carbohydrate fermenters; for the presence of colonies having a second color, contrasting with said first color, and having said third colored zone discernable and distinguishable thereabout, such colonies being colonies of said second biological material, and being carbohydrate fermenters; and for the presence of colonies having said first color, and not having said second color or said third colored zone discernable and distinguishable therewith, such colonies being colonies of a third biological material; and enumerating each of said colonies.

2. The method of claim 1, including the step of further examining said test medium for the presence of colonies having a color other than said first and second colors, or being colorless, with or without said third colored zone, such colonies being colonies of at least a fourth biological material.

3. The method of claim 1, including the step of further examining said test medium for the presence of colonies not having either of said first and second colors, with or without the third colored zone, such colonies being colonies of at least a fourth biological material; and for the presence of colonies having a fourth color, with or without the third colored zone, such colonies being colonies of at least a fifth biological material.

4. The method of claim 1, wherein said first chromogenic substrate comprises 6-chloro-3-indolyl galactosidase, said second chromogenic substrate comprises 5-bromo-4-chloro-3-indolyl glucuronidase, said carbohydrate comprises sorbitol and said pH indicator comprises phenol red.

5. The method of claim 1, wherein the test medium further comprises at least one growth inhibitor.

6. The method of claim 5, wherein said at least one growth inhibitor comprises bile, sodium lauryl sulfate, sodium desoxycholate or polyglycol ether.

7. The method of claim 1, wherein the test medium further comprises at least one of acriflavine and antibiotics.

8. The method of claim 1, wherein the test medium further comprises a reaction inducer.

9. The method of claim 1, wherein said reaction takes place at an incubation temperature of 30°–40° C., and said incubation continues for 24–48 hours, and wherein said pH of the test medium is about 7.2.

10. A test medium for detecting the presence of specified biological materials in a test sample comprising a plurality of different biological materials, said test medium comprising:

a nutrient base medium;

a first chromogenic substrate capable of forming a water insoluble component of a first color upon reacting with an enzyme from a first biological material;

a second chromogenic substrate capable of forming a water insoluble compound of a color contrasting with said first color upon reacting with an enzyme from a second biological material;

a fermentable component capable of acidifying a portion of the test medium upon fermentation, said fermentable component comprising a carbohydrate, and said fermentation caused by carbohydrate-fermenting biological materials in said test sample; and a pH indicator for causing a third color to be formed upon reaction to said acidification, said third color comprising a colored zone around said carbohydrate-fermenting biological materials.

11. The test medium of claim 10, wherein said nutrient base medium comprises a solid, a gel, a solution for forming a solid or an absorbent substrate having nutrients absorbed thereto.

12. The test medium of claim 10, wherein said nutrient base medium comprises a gelling agent selected from the group consisting of agars, pectins, carrageenans, alginates, locust bean, xanthin, guar and gellen.

13. The test medium of claim 10, wherein said test medium further comprises an enzyme inducer.

14. The test medium of claim 10, wherein said test medium includes a growth inhibitor.

15. The test medium of claim 10, wherein said first chromogenic substrate comprises a β-galactoside, said second chromogenic substrate comprises a β-glucuronide, said fermentable component comprises sorbitol, and said pH indicator comprises phenol red.

16. The test medium of claim 10, wherein said nutrient base medium comprises peptones.

17. A method for detecting the presence of and quantitatively identifying and differentiating E. coli 0157, other E. coli strains not including E. coli 0157, general coliforms and non-coliform Enterobacteriaceae in a test sample, comprising the steps of:

providing a test medium capable of forming a matrix or a solid surface with said test sample, said test medium comprising a chromogenic β-galactoside capable of forming a water insoluble compound of a first color upon reacting with β-galactosidase; a chromogenic β-glucuronide capable of forming a second water insoluble compound of a color contrasting with said first color upon reacting with β-glucuronidase; a fermentable component capable of acidifying a portion of the medium upon fermentation, said fermentable component comprising sorbitol, and said fermentation caused by the action of sorbitol-fermenting components of said test sample with sorbitol; a pH indicator capable of causing a third color to be formed in response to said acidification, said third color comprising a colored zone around said sorbitol-fermenting components; and a nutrient base medium;

adjusting the pH of said test medium to a range conducive for color change of the pH indicator upon acidification of said portion of the medium;

inoculating said test medium with said test sample;

incubating said test medium under conditions conducive for growth of colonies of general coliforms having β-galactosidase activity but not β-glucuronidase activity, colonies of *E. coli* having both β-glucuronidase activity and β-galactosidase activity, colonies of *E. coli* 0157 having β-galactosidase activity but not β-glucuronidase activity, and colonies of non-coliform Enterobacteriaceae, to produce contrasting colored precipitates corresponding to said activity;

examining said test medium for the presence of colonies having said first color and having said third colored zone visibly discernable and distinguishable thereabout, said colonies being colonies of general coliforms having β-galactosidase activity but not β-glucuronidase activity, and being sorbitol fermenters; for the presence of colonies having a second color, and having said third colored zone discernable and distinguishable thereabout, said colonies being colonies of *E. coli* having both β-glucuronidase activity and β-galactosidase activity, and being sorbitol fermenters; for the presence of colonies having said first color, and not having said second color or said third colored zone discernable and distinguishable therewith, said colonies being colonies of *E. coli* 0157 having β-galactosidase activity but not β-glucuronidase activity, and being sorbitol non-fermenters; and for the presence of colonies not having either of said first and second colors, with or without said third colored zone discernable and distinguishable thereabout, said colonies being non-coliform Enterobacteriaceae having neither β-galactosidase activity nor β-glucuronidase activity; and enumerating each of said colonies.

18. The method of claim 17, wherein said non-coliform Enterobacteriaceae colonies having neither β-galactosidase activity nor β-glucuronidase activity are separately enumerated dependent upon the presence of said third colored zone discernable and distinguishable thereabout, said colonies having said third colored zone thereabout being substantially colonies of Salmonella, and said colonies not having said third colored zone thereabout being substantially colonies of Proteus.

19. The method of claim 18, wherein said test medium is further examined for the presence of colonies of a fourth color, with or without said third colored zone discernable and distinguishable thereabout, said colonies being substantially Shigella and some strains of Salmonella.

20. The method of claim 17, wherein said chromogenic β-galactosidase substrate comprises 6-chloro-3-indolyl galactosidase.

21. The method of claim 17, wherein said chromogenic β-glucuronidase substrate comprises 5-bromo-4-chloro-3-indolyl glucuronidase.

22. The method of claim 17, wherein said pH indicator is phenol red, and wherein the medium is adjusted to a pH of about 7.2.

23. The method of claim 17, wherein the test medium further comprises growth inhibitors.

24. The method of claim 23, wherein said inhibitors comprise at least one member selected from the group consisting of bile, sodium lauryl sulfate, sodium desoxycholate and polyglycol ether.

25. The method of claim 17, wherein the test medium further comprises at least one of acriflavine and antibiotics.

26. The method of claim 17, wherein said test medium further comprises a reaction inducer.

27. The method of claim 26, wherein said reaction inducer comprises isopropyl-β-D-thiogalactopyranoside.

28. The method of claim 22, wherein said reaction takes place at a temperature of 30°–40° C., and said incubation continues for 24–48 hours, and wherein the pH of said test medium is about 7.2.

29. The method of claim 17, wherein said nutrient medium comprises a solid, a gel or a solution for forming a solid.

30. The method of claim 29, wherein the nutrient medium forms a solid support from a gelling agent, said gelling agent selected from the group consisting of agar and pectin.

31. A test medium for detecting the presence of *E. coli* 0157, other *E. coli* strains not including *E. coli* 0157, general coliforms and non-coliform Enterobacteriaceae in a test sample, comprising:

a nutrient base medium, said nutrient base medium comprising a solid, a gel or a solution for forming a solid;

a chromogenic β-galactosidase substrate capable of forming a water insoluble component of a first color upon reacting with β-galactosidase, said chromogenic β-galactosidase substrate selected from the group consisting of 6-chloroindolyl-β-D-galactoside, 5-bromo-6-chloro-3-indolyl-β-D-galactoside, 6-chloro-3-indolyl-β-D-galactoside, 4,6-dichloroindolyl-β-D-galactoside, 6,7-dichloroindolyl-β-D-galactoside, 4,6,7-trichloroindolyl-β-D-galactoside, 2-naphthyl-β-D-galactoside, and salts thereof;

a chromogenic β-glucuronidase substrate capable of forming a water insoluble component of a color contrasting with said first color upon reacting with β-glucuronidase, said chromogenic β-glucuronidase substrate selected from the group consisting of 5-bromo-4-chloro-3-indolyl-β-D-glucuronide, indoxyl-β-D-glucuronide, 4-chloro-3-indolyl-β-D-glucuronide, 5-bromo-3-indolyl-β-D-glucuronide and N-methyl-3-indolyl-β-D-glucuronide, and salts thereof;

a pH indicator; and sorbitol.

32. The test medium of claim 31, wherein said nutrient base medium comprises a gelling agent selected from the group consisting of agars, pectins, carrageenans, alginates, locust bean, xanthin, guar and gellen.

33. The test medium of claim 31, wherein said test medium further comprises an enzyme inducer.

34. The test medium of claim 33, wherein said enzyme inducer comprises isopropyl-β-D-thiogalactopyranoside.

35. The test medium of claim 31, wherein said pH indicator is phenol red.

36. The test medium of claim 31, wherein said medium includes an inhibitor selected from the group consisting of bile salts, sodium lauryl sulfate, sodium desoxycholate, polyglycol ethers and mixtures thereof.

* * * * *